US011344827B2

(12) United States Patent
Rhodes

(10) Patent No.: US 11,344,827 B2
(45) Date of Patent: May 31, 2022

(54) MICROCARRIER FILTER BAG ASSEMBLIES AND METHODS OF USE

(71) Applicant: LIFE TECHNOLOGIES CORPORATION, Carlsbad, CA (US)

(72) Inventor: Charles R. Rhodes, Preston, ID (US)

(73) Assignee: Life Technologies Corporation, Carlsbad, CA (US)

(*) Notice: Subject to any disclaimer, the term of this patent is extended or adjusted under 35 U.S.C. 154(b) by 131 days.

(21) Appl. No.: 16/820,007

(22) Filed: Mar. 16, 2020

(65) Prior Publication Data

US 2020/0282343 A1     Sep. 10, 2020

Related U.S. Application Data

(62) Division of application No. 15/827,938, filed on Nov. 30, 2017, now Pat. No. 10,589,197.

(Continued)

(51) Int. Cl.
*B01D 29/27* (2006.01)
*C12M 1/12* (2006.01)
(Continued)

(52) U.S. Cl.
CPC ............ *B01D 29/27* (2013.01); *C12M 23/14* (2013.01); *C12M 23/28* (2013.01); *C12M 25/16* (2013.01);
(Continued)

(58) Field of Classification Search
CPC ...... B01D 29/27; B01D 35/027; C12M 25/16; C12M 23/28; C12M 29/04; C12M 23/14; C12M 33/14; C12M 47/02
(Continued)

(56) References Cited

U.S. PATENT DOCUMENTS 1,269,189 A    6/1918 Kadish
1,471,332 A    10/1923 Greenawalt
(Continued)

FOREIGN PATENT DOCUMENTS

CA         2214384      10/1996
CH         675368 A5    9/1990
(Continued)

OTHER PUBLICATIONS

International Search Report and Written Opinion dated Mar. 6, 2018, issued in PCT Application No. PCT/US2017/063985, filed Nov. 30, 2017.
(Continued)

*Primary Examiner* — Madeline Gonzalez
(74) *Attorney, Agent, or Firm* — Workman Nydegger

(57) ABSTRACT

A filter bag assembly includes a flexible bag bounding a compartment that is configured to hold a fluid. An inlet port and an outlet port are each secured to the flexible bag so as to communicate with the compartment. A porous filter sheet is disposed within the compartment of the flexible bag so that fluid entering the compartment through the inlet port must pass through the filter sheet before exiting the compartment through the outlet port. A first retention seal secures the porous filter sheet to a portion of the flexible bag within the compartment, the first retention seal having an outer perimeter edge that forms an annular continuous loop.

16 Claims, 9 Drawing Sheets

Related U.S. Application Data

(60) Provisional application No. 62/428,961, filed on Dec. 1, 2016.

(51) Int. Cl.
  *C12M 1/00* (2006.01)
  *C12M 1/26* (2006.01)
  *B01D 35/027* (2006.01)

(52) U.S. Cl.
  CPC ............ *C12M 29/04* (2013.01); *C12M 33/14* (2013.01); *C12M 47/02* (2013.01); *B01D 35/027* (2013.01)

(58) Field of Classification Search
  USPC ........ 210/645, 448, 450, 451, 490, 483, 446
  See application file for complete search history.

(56) References Cited

U.S. PATENT DOCUMENTS

| | | |
|---|---|---|
| 1,505,204 A | 8/1924 | Kiernan |
| 2,259,243 A | 10/1941 | Daman |
| 2,341,114 A | 2/1944 | Novak |
| 2,865,618 A | 12/1958 | Abell |
| 3,074,544 A | 1/1963 | Bollmeier et al. |
| 3,184,395 A | 5/1965 | Brewer |
| 3,207,420 A | 9/1965 | Navarrete-Kindelan |
| 3,445,237 A | 5/1969 | Gidge |
| 3,545,671 A | 12/1970 | Ross |
| 3,608,709 A | 9/1971 | Pike |
| 3,647,397 A | 3/1972 | Coleman |
| 3,682,168 A | 8/1972 | Deaton |
| 3,701,433 A | 10/1972 | Krakauer |
| 3,702,619 A | 11/1972 | Son |
| 3,796,417 A | 3/1974 | Kaelin |
| 4,012,471 A | 3/1977 | Kunkle, Jr. |
| 4,012,473 A | 3/1977 | Lindsey et al. |
| 4,025,590 A | 5/1977 | Igich |
| 4,036,919 A | 7/1977 | Komendowski et al. |
| 4,061,698 A | 12/1977 | Thornwald |
| 4,100,235 A | 7/1978 | Thornwald |
| 4,157,965 A | 6/1979 | Raible |
| 4,204,774 A | 5/1980 | de Bruyne |
| 4,250,039 A | 2/1981 | Cozzi et al. |
| 4,391,912 A | 7/1983 | Yoshida |
| 4,402,402 A | 9/1983 | Pike |
| 4,458,811 A | 7/1984 | Wilkinson |
| 4,465,645 A | 8/1984 | Kaelin |
| 4,493,637 A | 1/1985 | Ganter et al. |
| 4,558,811 A | 12/1985 | Klaus |
| 4,581,143 A | 4/1986 | Pepper |
| 4,588,554 A | 5/1986 | Kaartinen et al. |
| 4,668,632 A | 5/1987 | Young et al. |
| 4,684,486 A | 8/1987 | Ricchio |
| 4,727,040 A | 2/1988 | Freedman et al. |
| 4,740,202 A | 2/1988 | Stacey et al. |
| 4,749,654 A | 6/1988 | Karrer et al. |
| 4,814,124 A | 3/1989 | Aoyama et al. |
| 4,869,398 A | 9/1989 | Colvin et al. |
| 4,869,852 A | 9/1989 | Goudy, Jr. et al. |
| 4,981,623 A | 1/1991 | Ryan |
| 5,008,197 A | 4/1991 | Wergeland et al. |
| 5,023,119 A | 6/1991 | Yamakoshi |
| 5,057,429 A * | 10/1991 | Watanabe ............. B01F 9/0001 435/297.1 |
| 5,100,376 A | 3/1992 | Blake, III |
| 5,139,946 A | 8/1992 | Howell et al. |
| 5,183,595 A | 2/1993 | Schüssler |
| RE34,386 E | 9/1993 | Davidson et al. |
| 5,270,207 A | 12/1993 | Matsumura et al. |
| 5,287,961 A | 2/1994 | Herran |
| 5,376,271 A | 12/1994 | Morgan, Jr. |
| 5,416,022 A | 5/1995 | Amiot |
| 5,422,043 A | 6/1995 | Burris |
| 5,431,496 A | 7/1995 | Balteau et al. |
| 5,431,498 A | 7/1995 | Lyon |
| 5,443,985 A | 8/1995 | Lu et al. |
| 5,458,771 A | 10/1995 | Todd |
| 5,487,470 A | 1/1996 | Pharo |
| 5,547,108 A | 8/1996 | Gsell et al. |
| 5,565,015 A | 10/1996 | Kobayashi |
| 5,578,459 A | 11/1996 | Gordon |
| 5,635,387 A | 6/1997 | Fei |
| 5,653,794 A | 8/1997 | Weber |
| 5,693,537 A | 12/1997 | Wilson et al. |
| 5,714,384 A | 2/1998 | Wilson et al. |
| 5,763,267 A | 6/1998 | Kurjan |
| 5,788,661 A | 8/1998 | Japuntich |
| 5,799,830 A | 9/1998 | Carroll et al. |
| 5,858,015 A | 1/1999 | Fini |
| 5,858,283 A | 1/1999 | Burris |
| 5,897,997 A | 4/1999 | Louvel |
| 5,910,138 A | 6/1999 | Sperko et al. |
| 5,925,293 A | 7/1999 | Howk |
| 5,941,635 A | 8/1999 | Stewart |
| 6,017,598 A | 1/2000 | Kreischer et al. |
| 6,068,775 A | 5/2000 | Custer et al. |
| 6,071,005 A | 6/2000 | Ekambaram et al. |
| 6,083,587 A | 7/2000 | Smith et al. |
| 6,086,574 A | 7/2000 | Carroll et al. |
| 6,099,734 A | 8/2000 | Boggs |
| 6,117,801 A | 9/2000 | McGinty et al. |
| 6,146,875 A | 11/2000 | Ward |
| 6,186,932 B1 | 2/2001 | Vallot |
| 6,219,871 B1 | 4/2001 | Frederick et al. |
| 6,245,555 B1 | 6/2001 | Curtis |
| 6,250,796 B1 | 6/2001 | Huang |
| 6,251,295 B1 | 6/2001 | Johnson |
| H1989 H | 9/2001 | Fell et al. |
| 6,367,783 B1 | 4/2002 | Raftis |
| 6,391,638 B1 | 5/2002 | Shaaltiel |
| 6,398,195 B1 | 6/2002 | Sherman |
| 6,406,005 B1 | 6/2002 | Lawson et al. |
| 6,432,698 B1 | 8/2002 | Gaugler et al. |
| 6,439,756 B1 | 8/2002 | Forschner et al. |
| 6,464,211 B1 | 10/2002 | Downs |
| 6,468,792 B1 | 10/2002 | Bader |
| 6,494,613 B2 | 12/2002 | Terentiev |
| 6,518,057 B2 | 2/2003 | Morrison |
| 6,596,521 B1 | 7/2003 | Chang et al. |
| 6,632,658 B1 | 10/2003 | Schoeb |
| 6,642,019 B1 | 11/2003 | Anderson et al. |
| 6,649,405 B2 | 11/2003 | Alms et al. |
| 6,670,169 B1 | 12/2003 | Schöb et al. |
| 6,673,598 B1 | 1/2004 | Akers et al. |
| 6,709,862 B2 | 3/2004 | Curtis |
| 6,712,963 B2 | 3/2004 | Schink |
| 6,745,902 B2 | 6/2004 | Lunn et al. |
| 6,884,866 B2 | 4/2005 | Bronshtein et al. |
| 6,908,223 B2 | 6/2005 | Bibbo et al. |
| 6,923,567 B2 | 8/2005 | Bibbo et al. |
| 6,969,367 B2 | 11/2005 | Hosheng |
| 7,141,203 B2 | 11/2006 | Way et al. |
| 7,198,225 B2 | 4/2007 | Chiba |
| 7,278,780 B2 | 10/2007 | Goodwin et al. |
| 7,326,355 B2 | 2/2008 | Graetz et al. |
| 7,384,027 B2 | 6/2008 | Terentiev et al. |
| 7,384,783 B2 | 6/2008 | Kunas et al. |
| 7,390,652 B2 | 6/2008 | Condon |
| 7,431,837 B2 | 10/2008 | Cohee et al. |
| 7,448,601 B2 | 11/2008 | Boer |
| 7,469,884 B2 | 12/2008 | Terentiev et al. |
| 7,629,167 B2 | 12/2009 | Hodge et al. |
| 7,681,867 B2 | 3/2010 | Hu et al. |
| 7,682,067 B2 | 3/2010 | West et al. |
| 7,879,599 B2 | 2/2011 | Goodwin |
| 7,935,101 B2 | 5/2011 | Muramatsu |
| 8,282,267 B2 | 10/2012 | Castillo et al. |
| 8,485,727 B2 | 7/2013 | Trouilly et al. |
| 8,603,805 B2 | 12/2013 | Goodwin et al. |
| 8,960,486 B2 | 2/2015 | Goodwin |
| 9,005,971 B2 | 4/2015 | Goodwin et al. |
| 9,079,690 B1 | 7/2015 | Pavlik |
| 9,259,692 B2 | 2/2016 | Goodwin et al. |

(56) References Cited

U.S. PATENT DOCUMENTS

| | | |
|---|---|---|
| 9,376,655 B2 | 6/2016 | Larsen |
| 9,643,133 B2 | 5/2017 | Goodwin et al. |
| 9,968,519 B2 | 5/2018 | Pavlik |
| 10,301,585 B2 | 5/2019 | Larsen |
| 2001/0031491 A1 | 10/2001 | Curtis |
| 2002/0063347 A1 | 5/2002 | Lee et al. |
| 2002/0131654 A1 | 9/2002 | Smith et al. |
| 2003/0036192 A1 | 2/2003 | Singh |
| 2003/0077466 A1 | 4/2003 | Smith et al. |
| 2003/0119185 A1 | 6/2003 | Berenson et al. |
| 2004/0058436 A1 | 3/2004 | Zhang |
| 2004/0062140 A1 | 4/2004 | Cadogan et al. |
| 2004/0095842 A1 | 5/2004 | Weetman |
| 2004/0134802 A1 | 7/2004 | Inoue et al. |
| 2004/0210288 A1 | 10/2004 | Karapetyan |
| 2005/0032205 A1 | 2/2005 | Smith |
| 2005/0158851 A1 | 7/2005 | Furey |
| 2005/0218075 A1 | 10/2005 | Graetz et al. |
| 2005/0239199 A1 | 10/2005 | Kunas et al. |
| 2005/0242114 A1 | 11/2005 | Savage et al. |
| 2005/0272146 A1 | 12/2005 | Hodge et al. |
| 2005/0282269 A1 | 12/2005 | Proulx |
| 2006/0054557 A1 | 3/2006 | Hori et al. |
| 2006/0196501 A1 | 9/2006 | Bibbo et al. |
| 2006/0270036 A1 | 11/2006 | Goodwin et al. |
| 2007/0037279 A1 | 2/2007 | Courtois et al. |
| 2008/0068920 A1 | 3/2008 | Galliher et al. |
| 2008/0139865 A1 | 6/2008 | Galliher et al. |
| 2008/0234654 A1 | 9/2008 | McCarthy et al. |
| 2008/0293133 A1 | 11/2008 | Reid et al. |
| 2009/0035856 A1 | 2/2009 | Galliher et al. |
| 2009/0113753 A1 | 5/2009 | Pepper et al. |
| 2009/0140005 A1 | 6/2009 | Reichert et al. |
| 2009/0180933 A1 | 7/2009 | Kauling et al. |
| 2010/0072216 A1 | 3/2010 | Voute et al. |
| 2010/0078395 A1 | 4/2010 | Shevitz |
| 2010/0174099 A1 | 7/2010 | Behkish |
| 2010/0264100 A1 | 10/2010 | Rivera |
| 2010/0310548 A1 | 12/2010 | Yeh |
| 2011/0013473 A1 | 1/2011 | Ludwig et al. |
| 2011/0014689 A1 | 1/2011 | Gandlur |
| 2011/0020922 A1 | 1/2011 | Wuenn et al. |
| 2011/0070648 A1 | 3/2011 | Anneren |
| 2011/0117538 A1 | 5/2011 | Niazi |
| 2012/0160763 A1* | 6/2012 | Yokomizo ............ A61M 1/3636 210/435 |
| 2012/0238011 A1 | 9/2012 | Tuohey et al. |
| 2012/0313267 A1 | 12/2012 | Pradel et al. |
| 2013/0081995 A1* | 4/2013 | Larsen ................. B01D 29/13 210/443 |
| 2013/0082410 A1 | 4/2013 | Goodwin et al. |
| 2013/0158635 A1 | 6/2013 | Federico et al. |
| 2015/0069072 A1 | 3/2015 | Kelley et al. |
| 2015/0118753 A1 | 4/2015 | Brau |
| 2015/0265758 A1 | 9/2015 | Verri |
| 2016/0244710 A1 | 8/2016 | Wood |
| 2016/0304825 A1 | 10/2016 | Larsen et al. |
| 2017/0197185 A1 | 7/2017 | Goodwin et al. |

FOREIGN PATENT DOCUMENTS

| | | |
|---|---|---|
| CN | 101696388 A | 4/2010 |
| CN | 101977673 A | 2/2011 |
| DE | 200 07 347 U1 | 8/2000 |
| DE | 202010013812 U1 | 2/2011 |
| EP | 0 343 885 A1 | 11/1989 |
| EP | 0725134 A2 | 7/1996 |
| EP | 1 602 715 A2 | 12/2005 |
| FR | 2 519 020 | 1/1983 |
| FR | 2 797 887 A1 | 3/2001 |
| FR | 2 799 138 | 4/2001 |
| GB | 2 202 549 A | 9/1988 |
| JP | S50-119561 | 9/1975 |
| JP | S58-224683 | 12/1983 |
| JP | S61-067476 | 4/1986 |
| JP | S62-160899 | 7/1987 |
| JP | H02-31825 | 2/1990 |
| JP | H02-283274 | 11/1990 |
| JP | H03-010675 | 1/1991 |
| JP | H03-242297 | 10/1991 |
| JP | H05-336957 | 12/1993 |
| JP | H06-153902 | 6/1994 |
| JP | H07-08264 | 1/1995 |
| JP | H07-155170 | 6/1995 |
| JP | H08-224076 | 9/1996 |
| JP | H10-099071 | 4/1998 |
| JP | S63-84483 | 4/1998 |
| JP | H10-150972 | 9/1998 |
| JP | H10-313718 | 12/1998 |
| JP | H11-502716 | 3/1999 |
| JP | H11-299478 | 11/1999 |
| JP | 2001-258547 | 9/2001 |
| JP | 2002-101867 | 4/2002 |
| JP | 2007-511230 | 5/2007 |
| JP | 2008-536685 A | 9/2008 |
| RU | 2 220 917 C1 | 1/2004 |
| WO | 92/15491 A1 | 9/1992 |
| WO | 1996/30497 | 10/1996 |
| WO | 2001/25394 | 4/2001 |
| WO | 2002/41484 A2 | 5/2002 |
| WO | 2005/068059 A1 | 7/2005 |
| WO | 2005/118771 | 12/2005 |
| WO | 2006/116067 A1 | 11/2006 |
| WO | 2007/134267 A2 | 11/2007 |
| WO | 2008/040568 A1 | 4/2008 |
| WO | 2008/157181 A1 | 12/2008 |
| WO | 2009/115241 | 9/2009 |
| WO | 2009/153425 | 12/2009 |
| WO | 2011/025890 A1 | 3/2011 |
| WO | 2011/079165 A1 | 6/2011 |
| WO | 2012/158108 A1 | 11/2012 |
| WO | 2013/049692 A1 | 4/2013 |

OTHER PUBLICATIONS

DuPont Medical Packaging, Technical Reference Guide for Medical Packaging, The Miracles of Science, 2002.

* cited by examiner

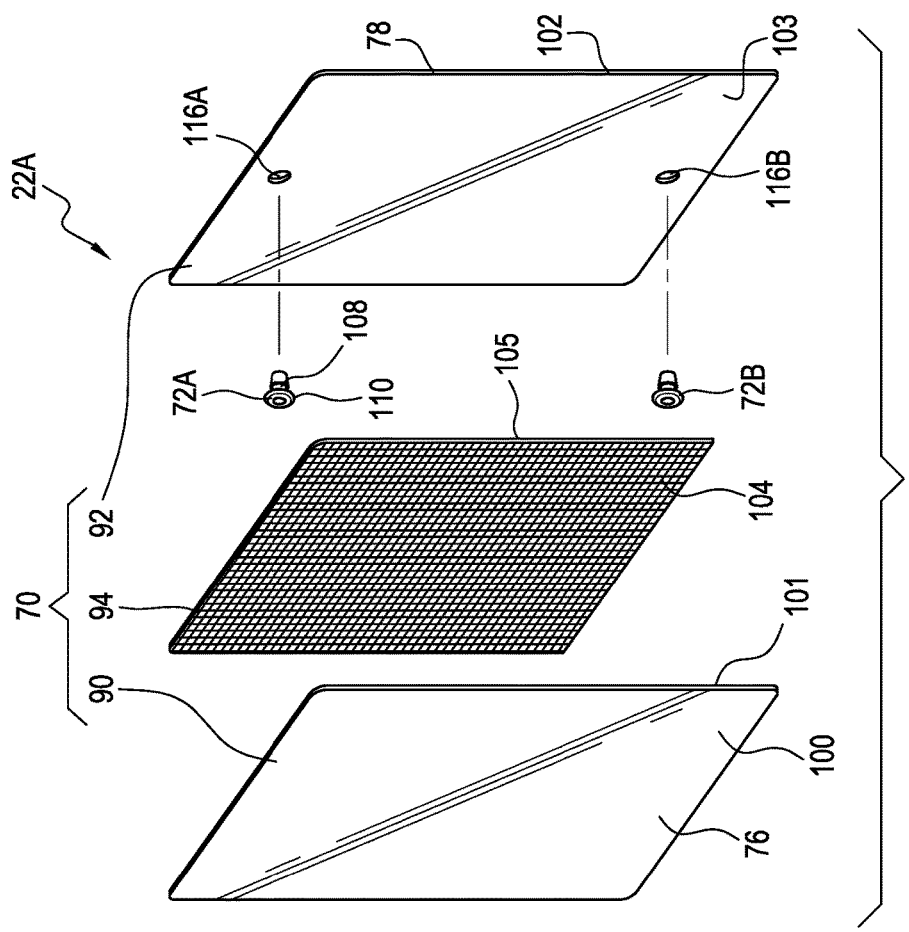
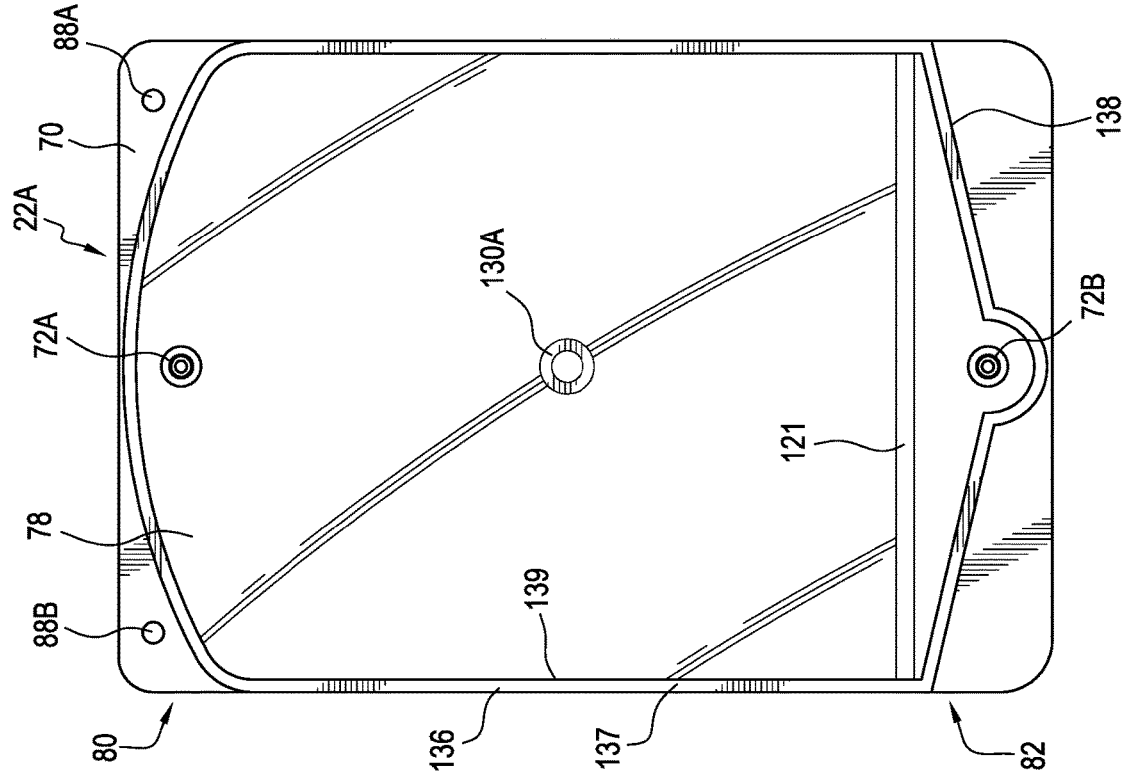
FIG. 7
FIG. 6

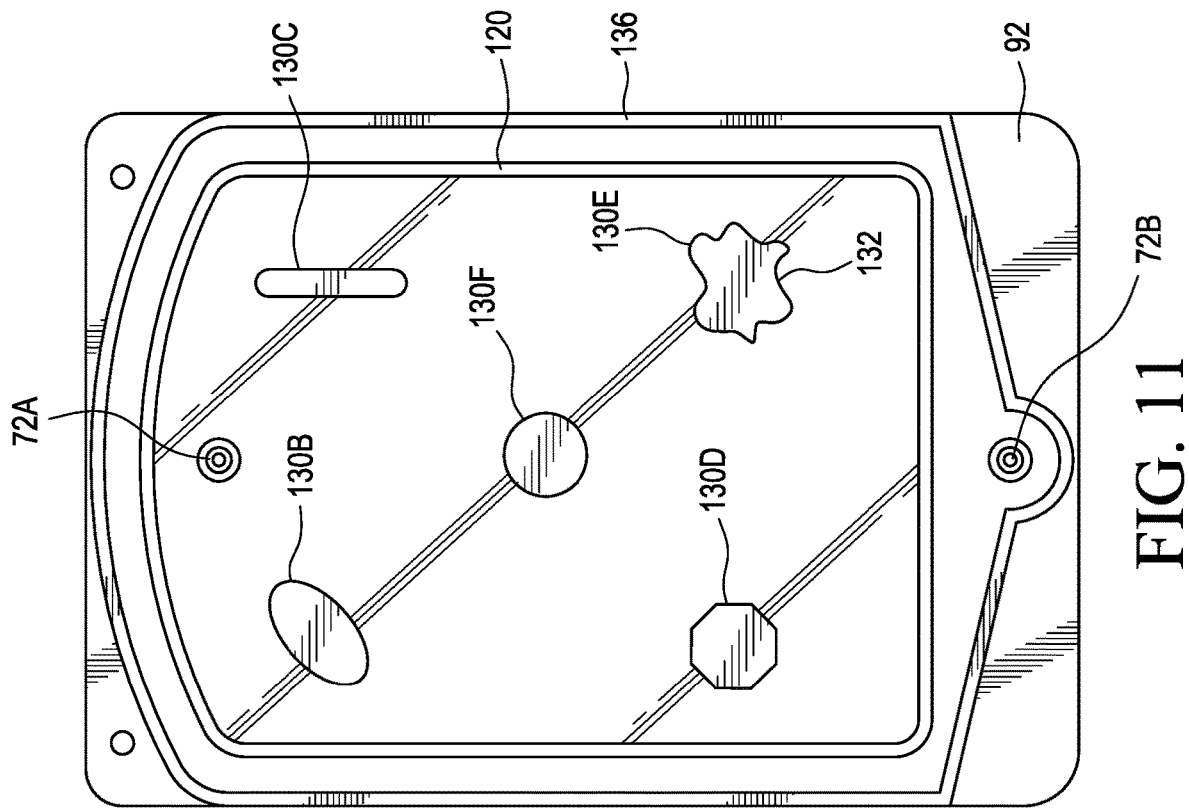
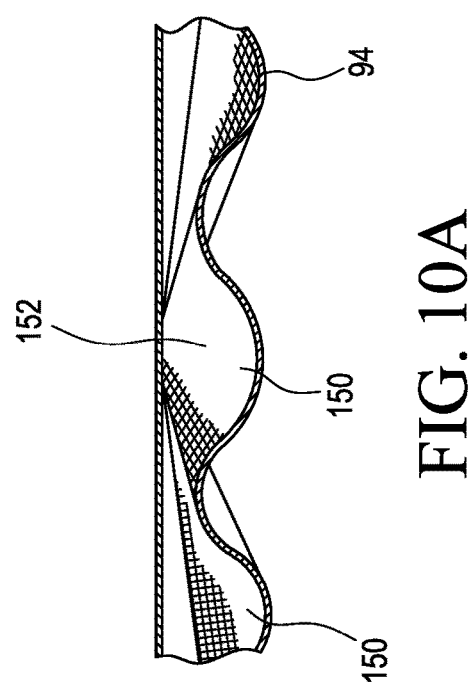
FIG. 10A
FIG. 11

MICROCARRIER FILTER BAG ASSEMBLIES AND METHODS OF USE

CROSS-REFERENCE TO RELATED APPLICATIONS

This application is a divisional of U.S. application Ser. No. 15/827,938, filed Nov. 30, 2017, which claims the benefit of U.S. Provisional Application No. 62/428,961, filed Dec. 1, 2016, which are incorporated herein by specific reference.

BACKGROUND OF THE INVENTION

1. The Field of the Invention

The present invention relates to filter systems and assemblies for separating microcarriers from cell culture solutions.

2. The Relevant Technology

The biopharmaceutical industry commonly uses microcarriers in the growth of anchorage-dependent cells. Specifically, microcarriers are regularly used during cell culturing to optimize growth of various anchorage-dependent cell lines, such as protein-producing or virus-generating adherent cell populations, which are commonly used in the production of biologics (proteins) and vaccines.

Microcarriers have a surface chemistry that allows for the attachment and growth of the anchorage dependent cells thereon in the cell culture procedure. Microcarriers can be made from a number of different materials and typically have a density that allows them to be maintained in suspension with only gentle stirring.

Microcarrier cell culturing is typically carried out in a bioreactor. During culturing, the cells grow on the surface of the microcarriers. Once the cell culturing process is completed, the cultured cells are detached from the microcarriers through a chemical process carried out in the solution. The cultured solution containing the cells is then separated from the microcarriers for use or further processing. The gathered microcarriers can be cleaned, sterilized, and re-used, or can be discarded.

Separation of the microcarriers from the cultured solution, which includes the detached cells, is typically achieved by passing the solution through a rigid container having a horizontal screen that extends across the rigid container. The screen is a rigid mesh that allows the cultured fluid to pass through but prevents the microcarriers from doing so. However, as the microcarriers build up on the screen, they begin to clog the screen and prevent the fluid from passing therethrough. Once the screen is clogged, the process stops until the screen is unclogged. Furthermore, once the process is completed, the rigid container and related screen must be cleaned and sterilized before it can be reused. These process steps can be expensive and time consuming.

Accordingly, what is needed in the art are methods and/or systems that can alleviate one or more of the above problems.

SUMMARY OF THE INVENTION

In a first independent aspect of the present invention, a filter bag assembly comprises:
a flexible first sheet;
a flexible second sheet overlying and secured to the first sheet so that a compartment is formed therebetween;
at least one port secured to the first sheet or the second sheet so as to communicate with the compartment;
a porous filter sheet disposed between the first sheet and second sheet, wherein the porous filter sheet is configured to filter a fluid entering the compartment; and
a first retention seal securing the second sheet to the filter sheet so that at least a portion of the compartment encircles the first retention seal.

In one example, the filter sheet divides the compartment into a pre-filter compartment and a post-filter compartment, the pre-filter compartment encircling the first retention seal.

In another example, an outlet port is secured to the first sheet or the second sheet, the at least one port comprising an inlet-port communicating with the pre-filter compartment and the outlet portion communicating with the post-filter compartment.

In another example, a first seal line secures the first sheet to the second sheet, the retention seal being spaced apart from the first seal line.

In another example, the first seal line forms a continuous loop.

In another example, a second seal line is formed between the filter sheet and the second sheet, the second seal line being in the form of a continuous loop that encircles the inlet port and the retention seal, a first portion of the second seal line comprising a portion of the first seal line and a second portion of the second seal line being spaced apart from the first seal line.

In another example, the filter bag assembly further includes:
a first seal line securing the first sheet to the second sheet and forming a continuous loop; and
a second seal line securing the filter sheet to the second sheet, the second seal line being in the form of a continuous loop that encircles the inlet port and the retention seal, the second seal line being spaced apart from the first seal line.

In another example, the first sheet and the second sheet comprise separate portions of a single continuous sheet that is folded over.

In one example, the porous filter sheet is disposed so that fluid entering the compartment through the inlet port must pass through the filter sheet before exiting the compartment through the outlet port.

In another example, the first retention seal has an annular outer perimeter edge.

In another example, the first retention seal is circular.

In another example, the first retention seal has the configuration of a ring.

In another example, the first retention seal has a maximum radius from a center or centroid of the first retention seal that is at least or less than 0.25 cm, 0.5 cm, 1 cm, 2 cm, 3 cm, 5 cm, 10 cm, or 15 cm.

In another example, the first retention seal has a minimum radius from a center or centroid of the first retention seal that is at least or less than 0.25 cm, 0.5 cm, 1 cm, 2 cm, 3 cm, 5 cm, 10 cm, or 15 cm.

In another example, a second retention seal is spaced apart from the first retention seal and secures the second sheet to the filter sheet, at least a portion of the compartment encircling the second retention seal.

In another example, the first retention seal also seals the first sheet to the filter sheet.

In another example, the filter sheet overlays the inlet port but is spaced apart from the outlet port.

In another example, the first sheet and the second sheet each comprise a sheet of polymeric film.

In another example, the first retention seal causes the filter sheet to have a plurality of creases when the filter sheet is pushed away from the second sheet.

The first aspect of the invention may include any of the features, options and possibilities set out elsewhere in this document, including in the other aspect of the invention.

In a second independent aspect of the present invention, a filter system includes:
- a support disposed at an angle in a range between about 15° and 75° relative to the horizontal; and
- the filter bag assembly as recited in claim 1 disposed on the support tray.

In one example, a tube having a first end is connected to a bioreactor and an opposing second end is coupled to the inlet port of the bag assembly.

The second aspect of the invention may include any of the features, options and possibilities set out elsewhere in this document, including in the other aspect of the invention.

In a third independent aspect of the present invention, a filter bag assembly includes:
- a flexible bag bounding a compartment that is configured to hold a fluid;
- an inlet port and an outlet port each secured to the flexible bag so as to communicate with the compartment;
- a porous filter sheet disposed within the compartment of the flexible bag so that fluid entering the compartment through the inlet port must pass through the filter sheet before exiting the compartment through the outlet port; and
- a first retention seal securing the porous filter sheet to a portion of the flexible bag within the compartment, the first retention seal having an outer perimeter edge that forms an annular continuous loop.

In one example, the outer perimeter edge of the first retention seal is circular.

In another example, the first retention seal has the configuration of a ring.

In another example, the first retention seal has a maximum radius from a center or centroid of the first retention seal that is at least or less than 0.25 cm, 0.5 cm, 1 cm, 2 cm, 3 cm, 5 cm, 10 cm, or 15 cm.

In another example, the first retention seal has a minimum radius from a center or centroid of the first retention seal that is at least or less than 0.25 cm, 0.5 cm, 1 cm, 2 cm, 3 cm, 5 cm, 10 cm, or 15 cm.

In another example, a second retention seal is spaced apart from the first retention seal and secures the porous filter sheet to a portion of the flexible bag.

In another example, the flexible bag comprises a flexible first sheet and a flexible second sheet that are secured together by a first seal line that encircles the compartment, the first retention seal being spaced apart from the first seal line.

In another example, the porous filter sheet is secured to the second sheet by a second seal line that encircles a portion of the porous filter sheet, the first retention seal being spaced apart from the second seal line.

In another example, the first seal line is spaced apart from the second seal line or at least a portion of the second seal line forms a portion of the first seal line.

In another example, the retention seal is formed on the portion of the porous filter sheet encircled by the second seal line.

In another example, the first sheet and the second sheet each comprise a sheet of polymeric film.

The third aspect of the invention may include any of the features, options and possibilities set out elsewhere in this document, including in the other aspect of the invention.

In a fourth independent aspect of the present invention, a method for filtering microcarriers from a liquid solution comprising cells includes:
- delivering the liquid solution with the microcarriers into a compartment of a filter bag assembly, the filter bag assembly comprising:
  - a flexible bag bounding the compartment;
  - a porous filter sheet disposed within the compartment of the flexible bag; and
  - a first retention seal securing a portion of the porous filter sheet to a portion of the flexible bag within the compartment; and
- passing the liquid solution through the porous filter sheet within the compartment of the flexible bag, the porous filter sheet being configured so that the microcarriers cannot pass therethrough, wherein as the microcarriers are collected within the compartment of the filter bag, the filter bag expands so that a plurality of creases are formed on the filter sheet.

In one example, the creases radially outwardly project from the first retention seal.

In another example, an outer perimeter edge of the first retention seal is circular.

In another example, the first retention seal has the configuration of a ring.

In another example, the first retention seal has a maximum radius from a center or centroid of the first retention seal that is at least or less than 0.25 cm, 0.5 cm, 1 cm, 2 cm, 3 cm, 5 cm, 10 cm, or 15 cm.

In another example, the first retention seal has a minimum radius from a center or centroid of the first retention seal that is at least or less than 0.25 cm, 0.5 cm, 1 cm, 2 cm, 3 cm, 5 cm, 10 cm, or 15 cm.

In another example, a second retention seal is spaced apart from the first retention seal and secures the porous filter sheet to a portion of the flexible bag.

In another example, the flexible bag comprises a flexible first sheet and a flexible second sheet are secured together by a first seal line that encircles the compartment, the first retention seal being spaced apart from the first seal line.

In another example, the porous filter sheet is secured to the second sheet by a second seal line that encircles a portion of the porous filter sheet, the first retention seal being spaced apart from the second seal line.

In another example, at least a portion of the compartment of the flexible bag encircles the retention seal.

The fourth aspect of the invention may include any of the features, options and possibilities set out elsewhere in this document, including in the other aspect of the invention.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 6 is a bottom plan view of the bag assembly shown in FIG. 5;

FIG. 7 is an exploded perspective view of the bag assembly shown in FIG. 6;

FIG. 10A is a cross sectional view of the filter sheet shown in FIG. 10 taken along lines 10A-10A;

FIG. 11 is a bottom plan view of the bag assembly shown in FIG. 6 showing a variety of alternative retention seals formed thereon;

DETAILED DESCRIPTION OF THE PREFERRED EMBODIMENTS

Figure 1:
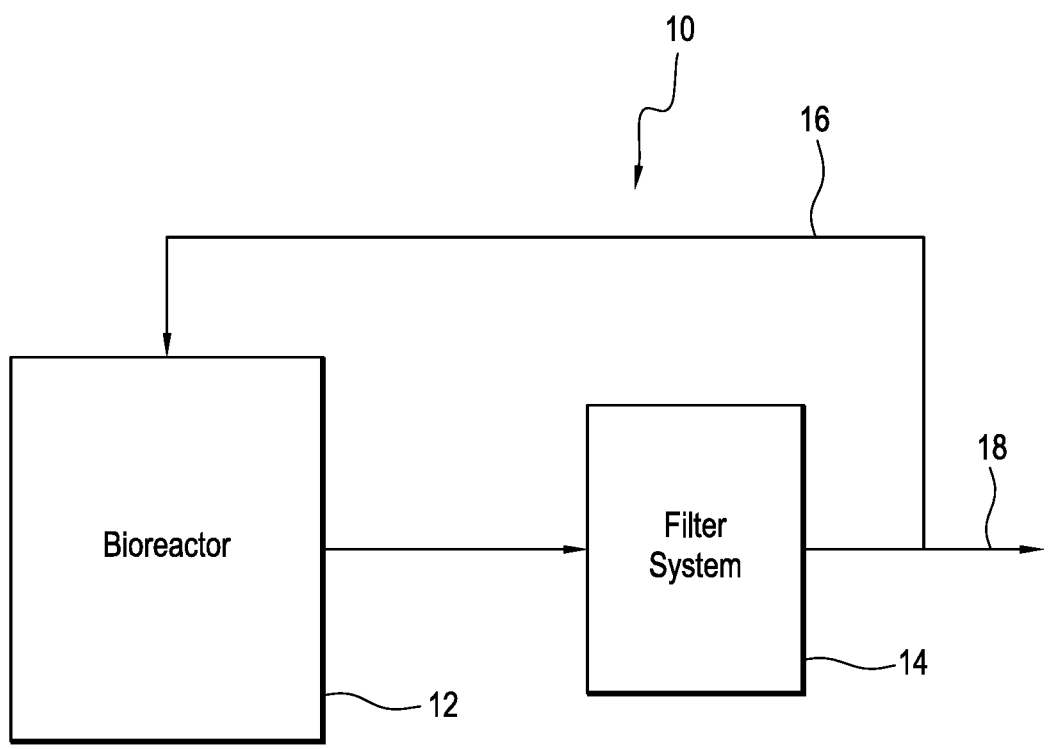
FIG. 1 is a schematic representation of a bioreactor that is fluid coupled to a filter system.

Before describing the present disclosure in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "retention seal" includes one, two, or more retention seals.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "210.") Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

The present invention relates to various apparatuses and methods for effectively filtering microcarriers or other particulates out of a cell culture solution while minimizing clogging or otherwise impeding the flow of the solution away from the microcarriers.

FIG. 1 depicts a cell culturing system 10 that incorporates features of the present invention. In cell culturing system 10, cells are grown within a biological container, such as bioreactor 12. Bioreactor 12 can be a microgravity bioreactor, internally-stirred bioreactor, fluidized bed bioreactor, rocker bag bioreactor or any other type of bioreactor known in the art. Bioreactor 12 can also be a rigid tank bioreactor that needs to be sterilized between uses or a single use bioreactor that includes a disposable bag. Other types of bioreactors or other biological containers can alternatively be used, such as, e.g., a spinner flask. The cells are grown in a nutrient growth medium that can include a variety of different components. The components are typically dependent on the cell type and processing conditions. Growth mediums and related components are known in the art and are not discussed herein.

Microcarriers are added to the growth medium within bioreactor 12 so that anchorage-dependent cells can grow thereon. The microcarriers can be spherically shaped beads typically ranging between about 130 microns to about 300 microns in diameter. Other sizes can also be used. It is also appreciated that the microcarriers can have alternative shapes but typically have a maximum diameter that is typically at least or smaller than 130 microns, 170 microns, 200 microns, 250 microns, 300 microns or in a range between any two of the foregoing. The microcarriers have a density that allows them to be maintained in suspension with gentle stirring. For example, the microcarriers can also have a density of that is typically at least or smaller than 1.0 g/cm$^3$, 1.02 g/cm$^3$, 1.05 g/cm$^3$, 1.10 g/cm$^3$, or 1.20 g/cm$^3$ or in a range between any two of the foregoing. Other densities are also possible. The microcarriers can be made from a number of different materials including DEAE-dextran, glass, polystyrene plastic, acrylamide, and collagen. The different types of microcarriers can differ in their porosity, specific gravity, optical properties, presence of animal components, and surface chemistries. Surface chemistries can include extracellular matrix proteins, recombinant proteins, peptides, and positively or negatively charged molecules. The microcarrier materials, along with the different surface chemistries, can influence cellular behavior, including morphology, proliferation and adhesion.

During culturing, the cells grow on the surface of the microcarriers disposed within the mixture. Once the cell culturing process is completed, a chemical reagent, such as an enzyme, is added to the mixture, which includes the growth medium, the microcarriers suspended within the growth medium, and the cells. The chemical reagent causes the cells to detach from the microcarriers so that the cells are freely suspended within the growth medium. The mixture is then removed from bioreactor 12 and passed through a filter system 14. As discussed below in greater detail, filter system 14 separates the microcarriers from the culture solution, which includes the growth medium and the detached cells. More specifically, the microcarriers can be captured by filter system 14 while the culture solution can freely pass through filter system 14. The culture solution can either be returned to bioreactor 12 through line 16 or transported downstream through line 18 to a further container or processing equipment either for packaging or further processing.

Figure 2:
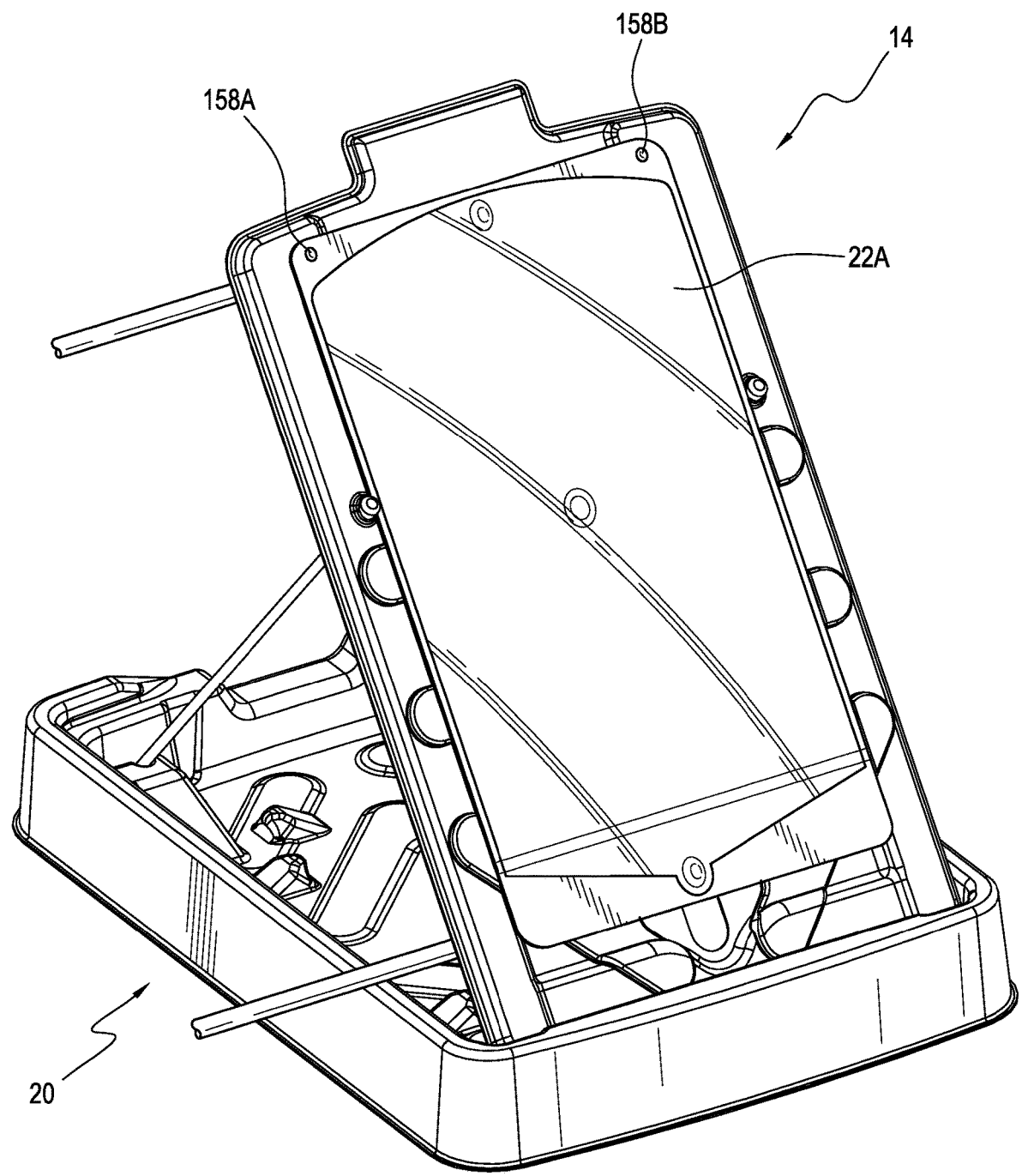
FIG. 2 is a front perspective view of one embodiment of the filter system shown in FIG. 1.
Figure 3:
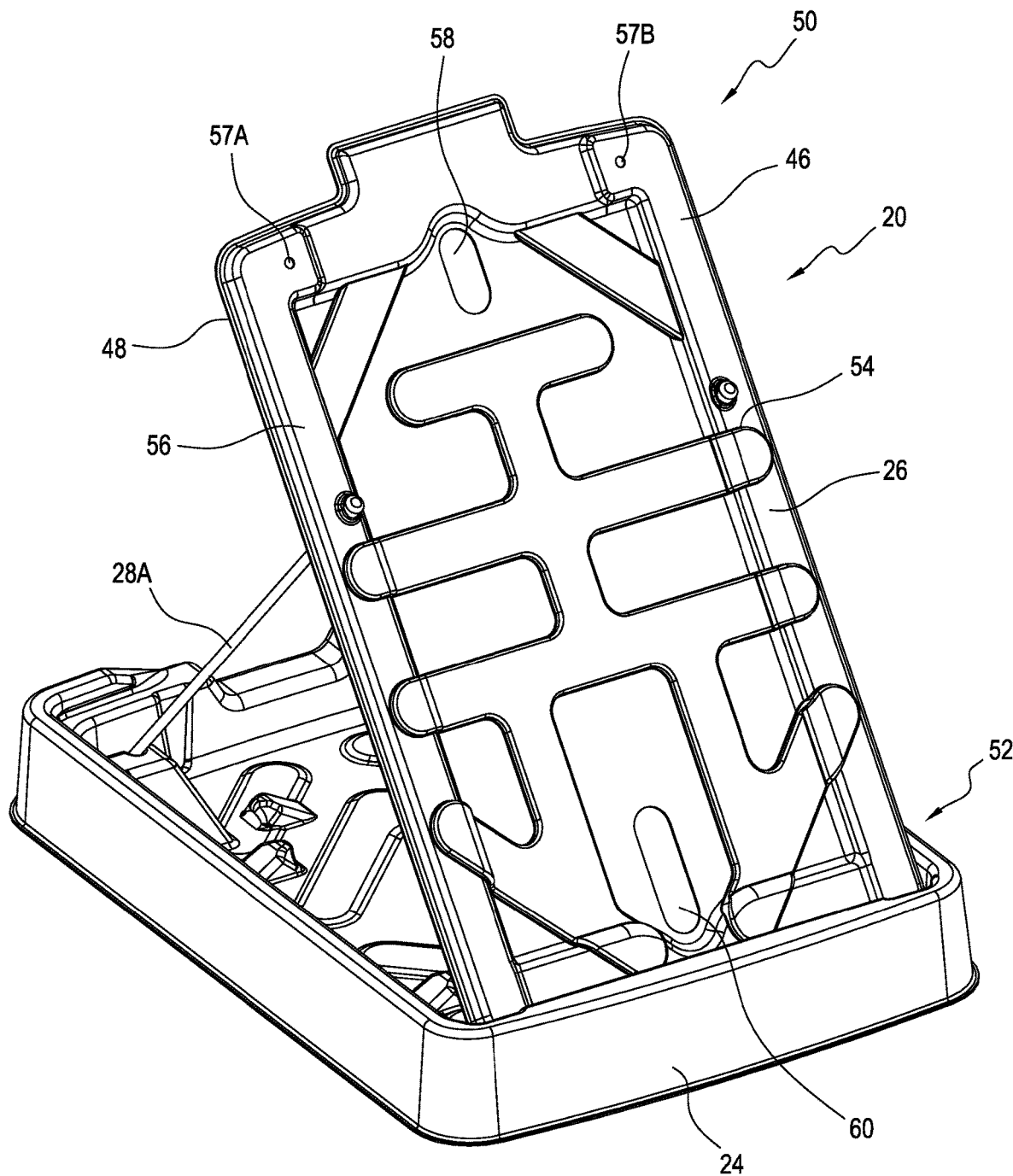
FIG. 3 is a front perspective view of a stand of the filter system shown in FIG. 2.
Figure 4:
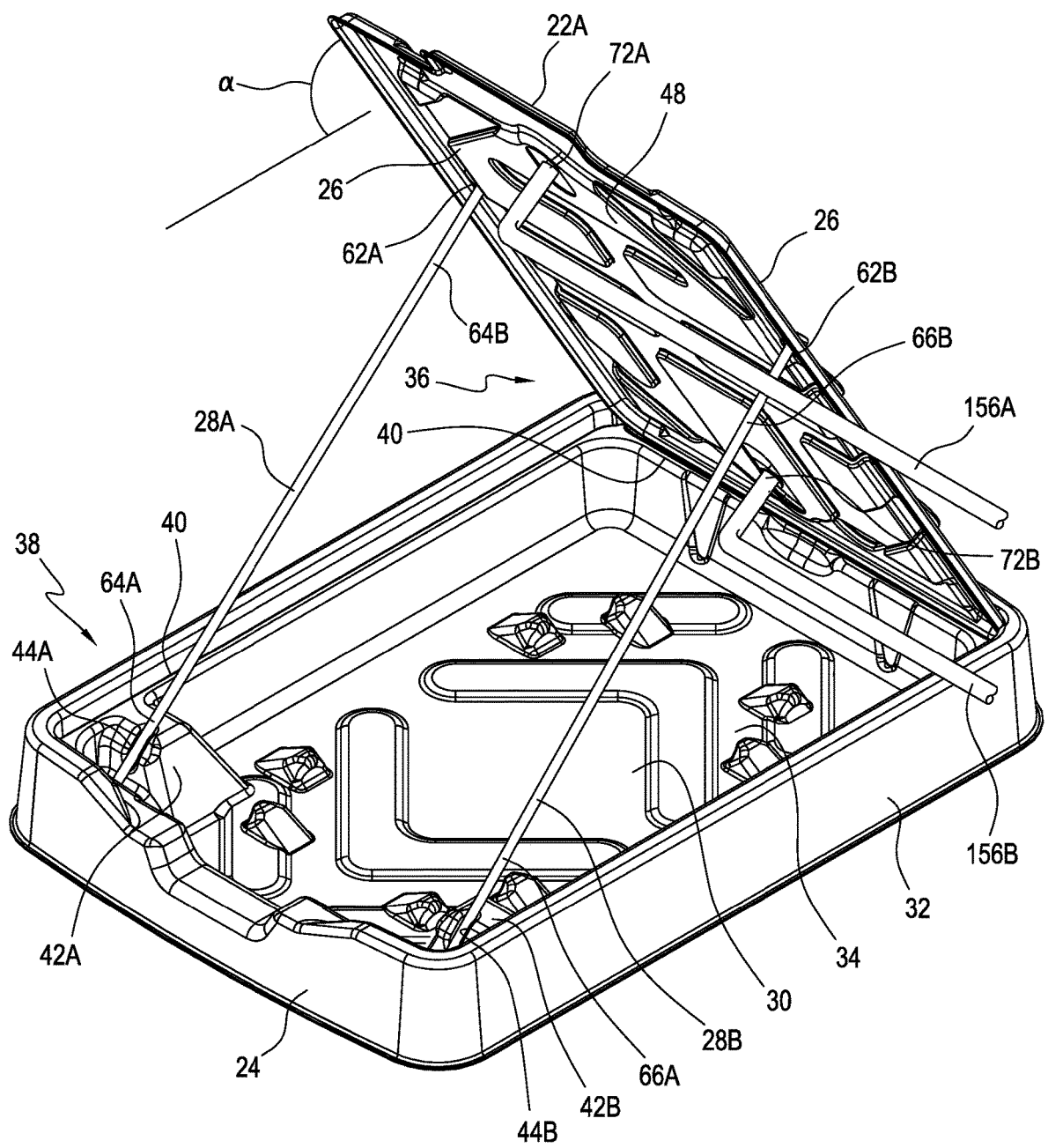
FIG. 4 is a rear perspective view of the filter system shown in FIG. 2.

As depicted in FIG. 2, filter system 14 comprises a stand 20 on which a filter bag assembly 22 is supported. As depicted in FIGS. 3 and 4, stand 20 comprises a tray 24, a support 26 upstanding on tray 24 and a pair of arms 28A and 28B that extend between tray 24 and support 26 so as to retain support 26 at a desired angle relative to horizontal. More specifically, tray 24 has a floor 30 having an upstanding perimeter side wall 32 extending therefrom. Floor 30 and perimeter side wall 32 partially bound a cavity 34. Tray 24 is elongated and extends between a first end 36 and opposing second end 38. A retention lip 40 is formed on and along perimeter side wall 32 above floor 30. A pair of braces 42A and 42B upstand from floor 30 at second end 38. A recess 44A and 44B is formed on each brace 42A and 42B.

Support 26 is in a form of a panel having a front face 46 and an opposing back face 48 that extend between a first end 50 and an opposing second end 52 and extend between a first side 54 and an opposing second side 56. A pair of spaced apart mounting holes 57A and 57B are recessed into or extend through support 26 at first end 50. A first opening 58 passes centrally through support 26 at first end 50 while a second opening 60 passes centrally through support 26 at second end 52. A pair of recesses 62A and 62B are recessed into back face 48 on first side 54 and second side 56, respectively, at or towards first end 50.

During use, second end 52 of support 26 is seated on retention lip 40 at first end 36 of tray 24. Arm 28A has a first end 64A received within cavity 34 and recess 44A of brace 42A and an opposing second end 64B received within recess 62A on support 26. Likewise, second arm 28B has a first end 66A received within cavity 34 and recess 44B of brace 42B and an opposing second end 66B disposed within recess 62B of support 26. In this orientation, when tray 24 is disposed on a horizontal surface, support 26 is disposed at an angle α relative to the horizontal that is typically in a range between 15° and 75° with between 25° and 65° or between 35° and 55° being more common. In other embodiments, the angle α can be at least or less than 15°, 35°, 45°, 55°, 65°, 75° or in a range between any two of the foregoing. The angle α can be changed by using arms 28 of different lengths or by using arms 28 that expand or contract, such as by telescoping. Thus, by lengthening arms 28 the angle α increases and by shortening the length of arms 28 the angle α decreases. When stand 20 is not in use, arms 28 can be removed from tray 24 and support 26 and stored within cavity 34. Support 26 can also be laid down to rest on lip 40 at least partially within cavity 34.

Figures 5, 8:
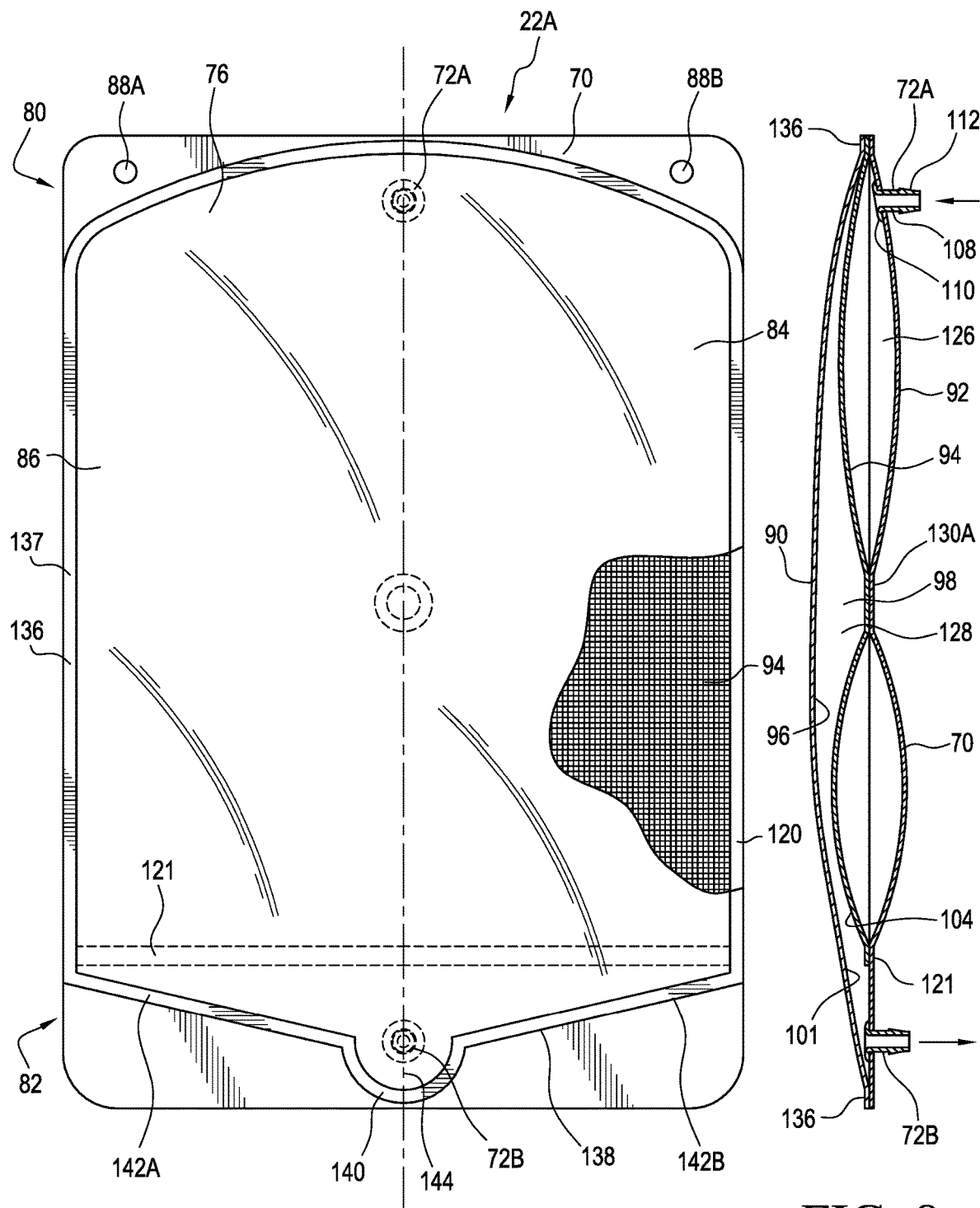
FIG. 5 is a top plan view of the bag assembly of the filter system shown in FIG. 2.
FIG. 8 is a cross sectional side view of the bag assembly shown in FIG. 5.

As depicted in FIGS. 5 and 6, bag assembly 22 comprises a bag 70 having a first port 72A and a second port 72B mounted thereon. Bag 70 has a front face 76 and an opposing back face 78 that extend between an upper end 80 and an opposing lower end 82 and also extend between a first side 84 and an opposing second side 86. A pair of spaced apart attachment holes 88A and 88B extend through bag 70 between faces 76 and 78 at upper end 80.

As depicted in FIG. 7, bag 70 is comprised of three sheets of material: a first sheet 90 that forms front face 76, a second sheet 92 that forms back face 78, and a filter sheet 94 that is sandwiched or otherwise disposed between sheets 90 and 92. First sheet 90 has an exterior surface 100 and an opposing interior surface 101; second sheet 92 has an exterior surface 102 and an opposing interior surface 103; and filter sheet 94 has front face 104 and an opposing back face 105.

Sheets 90 and 92 comprise a water impermeable polymeric film such as a low-density polyethylene. The polymeric film can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. The film is typically sufficiently flexible that it can be rolled into a tube without plastic deformation and/or can be folded over an angle of at least 90°, 180°, 270°, or 360° without plastic deformation.

The film can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. The laminated and extruded films typically have between 1-9 layers and more commonly between 3-9 layers. The films used can commonly have a number of layers that is at least or less than 1, 3, 5, 7, or 9 layers or in a range between any two of the foregoing. The extruded film can be a cast film such as a multi-layer co-extruded cast film. One example of an extruded material that can be used in the present invention is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Thermo Fisher Scientific. The Thermo Scientific CX5-14 cast film comprises a polyester elastomer outer layer, an ultra-low density polyethylene contact layer, and an EVOH barrier layer disposed therebetween.

The material can be approved for direct contact with living cells and be capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

As depicted in FIG. 8, bag 70 has an interior surface 96 that bounds a compartment 98 between first sheet 90 and second sheet 92. Compartment 98 typically has a volume of at least or less than 1 liter, 3 liters, 6 liters, 10 liters, 15 liters, 20 liters, 30 liters, 50 liters, 75 liters, 100 liters or in a range between any two of the foregoing. Other volumes can also be used.

Filter sheet 94 comprises a material that will allow the culture solution, i.e., growth medium and detached cells, to pass therethrough while preventing the microcarriers from passing therethrough. Filter sheet 94 can be comprised of a porous material such as a mesh, netting, perforated sheet, porous sheet, lattice type material, woven material, or any other material that will allow the culture solution to pass therethrough while preventing the associated microcarriers from passing therethrough. To enable the cells to pass through filter sheet 94 but prevent the microcarriers from passing therethrough, filter sheet 94 is typically made of a material having pores in the size of about 15 microns to about 100 microns, with about 30 microns to about 100 microns being common. If desired, filter sheet 94 can be expandable and/or resiliently stretchable. Examples of materials that can be used for filter sheet 94 include polyester (PET), polyamide (PA), polypropylene (PP), and polyetheretherketone (PEEK). Other materials, such as those used to form first sheet 90 and second sheet 92, discussed above, could also be used. It is also appreciated that filter sheet 94 can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. Filter sheet 94 is typically sufficiently flexible that it can be rolled into a tube without plastic deformation and can be folded over an angle of at least 90°, 180°, 270°, or 360° without plastic deformation. Filter sheet 94 and sheets 90 and 92 can be made from the same or different materials and can have the same or different melt temperatures.

Each port 72 has a tubular stem 108 having an annular flange 110 radially outwardly projecting from a first end and an annular tapered barb 112 formed on an opposing second end.

Figure 9:
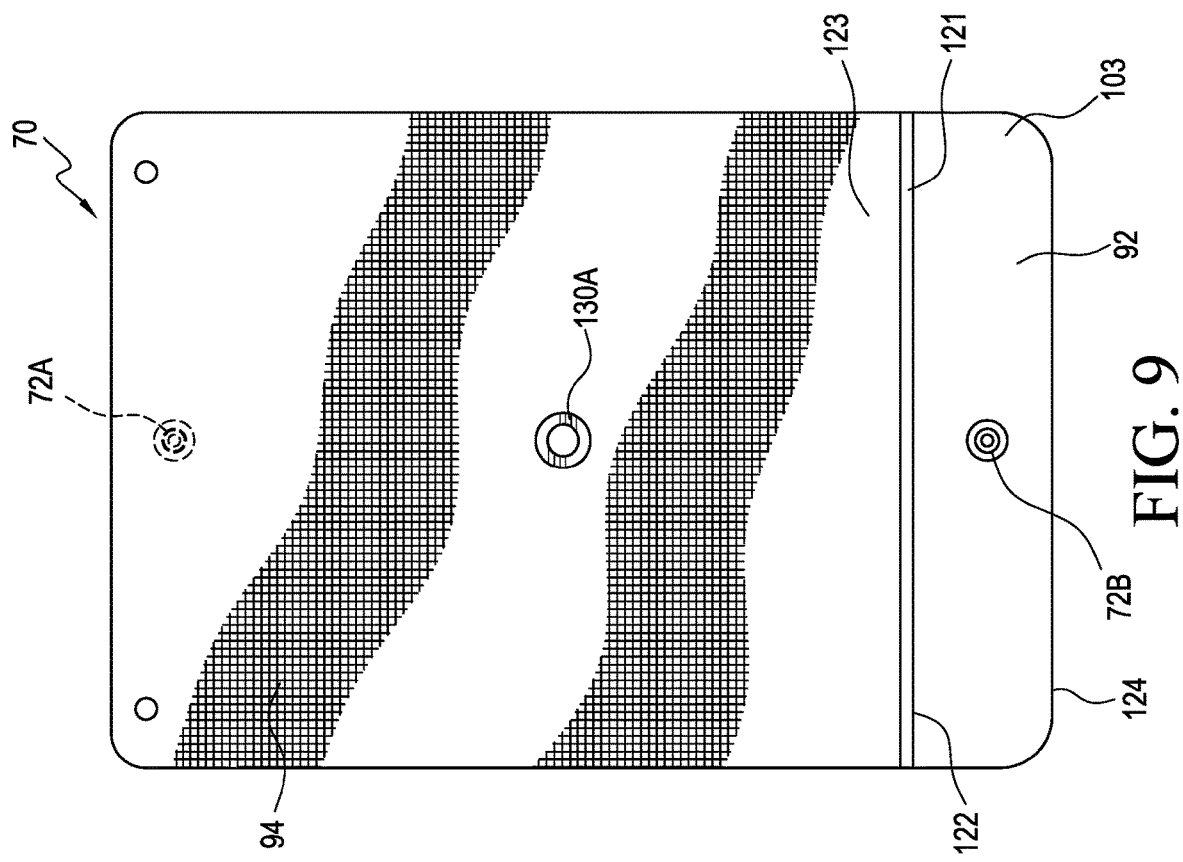
FIG. 9 is a top plan view of the filter sheet and back sheet of the bag assembly shown in FIG. 5 with the bag assembly empty.

During one example of formation of bag assembly 22, holes 116A and 116B, as depicted in FIG. 7, are centrally formed on second sheet 92 at the opposing ends thereof. Stems 108 of ports 72A and 72B are passed through holes 116A and 116B, respectively, from interior surface 103 of second sheet 92. Flanges 110 are then secured to interior surface 103 of second sheet 92 such as by welding or use of an adhesive. Next, back face 105 of filter sheet 94 is overlaid on top of interior surface 103 of second sheet 92 and the two sheets are partially secured together. Specifically, depicted in FIG. 9 is a top plan view showing filter sheet 94 overlaying and being partially secured to second sheet 92.

In this embodiment, filter sheet 94 is smaller than second sheet 92 and is positioned so that filter sheet 94 overlays first port 72A but does not overlay second port 72B. That is, filter sheet 94 has a bottom edge 122 disposed at a bottom end 123 that is upwardly spaced apart from a bottom edge 124 of second sheet 92 so that filter sheet 94 does not overlay but rather is spaced apart from second port 72B. Bottom edge 122 extends laterally to or toward the opposing side edges of second sheet 92. A seal line 121 is formed along bottom end 123, such as along bottom edge 122, so as to seal filter sheet 94 and second sheet 92 together. Seal line 121 can be formed by welding filter sheet 94 and second sheet 92 together through the application of heat energies, RF (radio frequency) energies, sonic energies, induction energies or other sealing energies, thereby forming a weld line. For example, where second sheet 92 has a lower melt temperature than filter sheet 94, energy can be applied to overlying sheets 92 and 94 until a portion of the interior surface of second sheet 92 melts and flows into and around the adjacent portion of filter sheet 94. Once the energy is removed and the melted plastic cools and solidifies, second sheet 92 and filter sheet 94 are sealed/welded together. In other embodiments, filter sheet 94 could have a lower melt temperature than second sheet 92 so that filter sheet 94 melts and bonds to second sheet 92. Likewise, both second sheet 92 and filter sheet 94 can have the same or substantially the same melt temperatures so that they both partially melt and bond to each other when energy is applied. In still other embodiments, a piece of polymeric material or other bonding material could be placed on top of filter sheet 94 or between filter sheet 94 and second sheet 92 so that when energy is applied, the piece of polymeric material or other bonding material partially or fully melts and seals/welds sheets 92 and 94 together with or without directly melting sheet 92 and/or sheet 94. In yet other embodiments, sealing line 121 can be formed through the application of an adhesive, a mechanical seal, such as a crimp, or by using other conventional sealing techniques.

As will also be discussed below, a retention seal 130A is also used to secure filter sheet 94 to second sheet 92. Retention seal 130A is spaced apart from seal line 121 and typically, although not required, is centrally formed on filter sheet 94. Retention seal 130A can be formed using the same techniques as seal line 121 discussed above, i.e., welding, adhesive, mechanical fastener and the like. In the depicted embodiment, retention seal 130A is circular and, more specifically, is in the form of a ring or donut. Where retention seal 130A has an outer perimeter edge that is circular, retention seal 130A will often have a radius that is at least or less than 0.25 cm, 0.5 cm, 1 cm 2 cm, 3 cm, 5 cm, 10 cm, 15 cm, or in a range between any two of the forgoing. Other dimensions can also be used. In alternative embodiments, it is appreciated that the retention seal need not be circular but can have a variety of different configurations. For example, in the embodiment depicted in FIG. 11, a retention seal 130B is formed having an oval or elliptical configuration; a retention seal 130C is formed that is linear; a retention seal 130C is formed that is polygonal, such as triangular, square, rectangular or other polygons having at least 5, 6, 7, 8, 9, or 10, sides; a retention seal 130E is formed have a perimeter edge 132 that is irregular or non-symmetrical; and a retention seal 130F is formed that is a sold circle in contrast to the ring of retention seal 130A. It is appreciated that retention seal(s) 130 can also have other shapes.

Where retention seal 130 has an outer perimeter that is non-circular, retention seal 130 can have a maximum radius extending from the centroid of retention seal 130 to the outer perimeter edge that is also at least or less than 0.25 cm, 0.5 cm, 1 cm 2 cm, 3 cm, 5 cm, 10 cm, 15 cm or in a range between any two of the foregoing. Likewise, retention seal 130 can have a minimum radius extending from the centroid of retention seal 130 to the outer perimeter edge that is at least or less than 0.25 cm, 0.5 cm, 1 cm 2 cm, 3 cm, 5 cm, 10 cm, 15 cm or in a range between any two of the foregoing. Other dimensions can also be used. The embodiment shown in FIG. 9 also illustrates that bag assembly 22 can be formed with a single retention seal 130. However, in other embodiments, such as in FIG. 11, bag assembly 22 can be formed with a plurality of spaced apart retention seals 130, such as at least or less than 2, 3, 4, 5, or 6 retention seals 130. The plurality of retention seals 130 can be the same shape and/or size or can be different shapes and/or sizes.

Returning to FIG. 8, after filter sheet 94 is secured to second sheet 92 at seal line 121 and retention seal 130A, interior surface 101 of first sheet 90 is overlaid on front face 104 of filter sheet 94 and is secured to the combination of filter sheet 94 and second sheet 92. First sheet 90 typically overlays all of filter sheet 94 and overlays second port 72B. A seal line 136, as shown in FIGS. 5 and 8, is now formed that generally extends around the perimeter of first sheet 90 and secures first sheet 90 to second sheet 92. Where filter sheet 94 is disposed between first sheet 90 and second sheet 92 along seal line 136, filter sheet 94 is also sealed/welded to sheets 90 and 92. Seal line 136 can be formed using the same techniques as seal line 121, discussed above. Seal line 136 forms a continuous loop that encircles first port 72A, second port 72B and retention seal 130. Seal line 136 also overlays and seals to the opposing ends of seal line 121. Seal line 136 includes an upper seal line portion 137 and a bottom seal line portion 138. Upper seal line portion 137 seals sheets 90, 92, and 94 together while bottom seal line portion 138 extends below filter sheet 94 and seals sheets 90 and 92 directly together while extending around second port 72B.

Bottom seal line portion 138 comprises a base 140 that curves below and partially around second port 72B in a substantially C- or U-shaped configuration so as to form a receptacle 144 that collect liquids around second port 72B. Bottom seal line portion 138 also includes a pair of arms 142A and 142B that slope down from the opposing sides of bag 70 and connect with the opposing sides of base 140 so as to direct fluid to receptacle 144 and second port 72B.

As a result of seal line 136, a pre-filter compartment 126, as shown in FIG. 8, is formed between filter sheet 94 and second sheet 92 where seal line 120 forms a perimeter edge of pre-filter compartment 126.

In the above assembly configuration, compartment 98 is bounded between sheets 90 and 92. Filter sheet 94 divides compartment 98 of bag 70 into a pre-filter compartment 126 and a post-filter compartment 128. Pre-filter compartment 126 is bounded directly between filter sheet 94 and second sheet 92 and has a perimeter edge in the form of a continuous loop formed by the combination of upper seal line portion 137 and seal line 121. As shown in FIG. 6, seal lines 137 and 121 combine to form a seal line 139. As such, pre-filter compartment 126 has a perimeter edge formed by a continuously encircling seal line 139 that secures filter sheet 94 to second sheet 92 and encircles first port 72A and retention seal 130A but does not encircle second port 72B. It is appreciated that the encircling seal line 139 need not be a circle but could be any desired shape that forms a continuous loop.

As depicted in FIG. 8, it is also noted that in this configuration that pre-filter compartment 126 encircles retention seal 130A. That is, as a result of retention seal 130A, pre-filter compartment 126 can have a toroid or donut shape that encircles retention seal 130A. Expressed in other terms, at least a portion of compartment 98 encircles retention seal 130A. The portion of compartment 98 that encircles retention seal 130A can comprise pre-filter compartment 126. Where two or more retention seals 130 are formed, as previously discussed, pre-filter compartment 126 can encircle each of the separate retention seals 130. In the assembled configuration, as discussed below in further detail, once the culture solution and the microcarriers are delivered into pre-filter compartment 126 by passing through first port 72A, the microcarriers are captured within pre-filter compartment 126 because they are stopped by seal line 139 and cannot pass through filter sheet 94. The culture solution, however, can pass through filter sheet 94.

Post-filter compartment 128 comprises the remainder of compartment 98 that does not include pre-filter compartment 126. More specifically, post-filter compartment 128 comprises the area bounded directly between first sheet 90 and filter sheet 94 and the area bounded directly between first sheet 90 and second sheet 92, i.e., the area where the cultured solution can flow after it passes through filter sheet 94 from pre-filter compartment 126. Accordingly, during use the culture solution and microcarriers pass through first port 72A and into pre-filter compartment 126. The microcarriers are captured and held within pre-filter compartment 126 by filter sheet 94 while the culture solution passes into post-filter compartment 128. The culture solution then travels downward within post-filter compartment 128 and exits out through second port 72B.

As microcarriers collect within pre-filter compartment 126, the microcarriers push filter sheet 94 toward first sheet 90. But for the formation of retention seal(s) 130, filter sheet 94 would be pushed against first sheet 90. In this configuration, the collected microcarriers would restrict or event prevent the flow of the culture solution into post-filter compartment 128 and/or to second port 72B. However, by forming retention seal(s) 130 at least a portion of filter sheet 94 held back against second sheet 92 and away from first sheet 90, as depicted in FIG. 8, thereby allowing post-filter compartment 128 to openly expand so that the culture solution can freely flow from pre-filter compartment 126 to post-filter compartment 128. Furthermore, one of the unique and surprising benefits of some embodiments of the present invention is that by forming retention seal(s) 130, a plurality of creases are formed in filter sheet 94 as microcarriers are collected within bag 70. The creases form fluid channels which allow the culture solution to freely pass between first sheet 90 and filter sheet 94 and flow to second port 72B.

Figure 10:
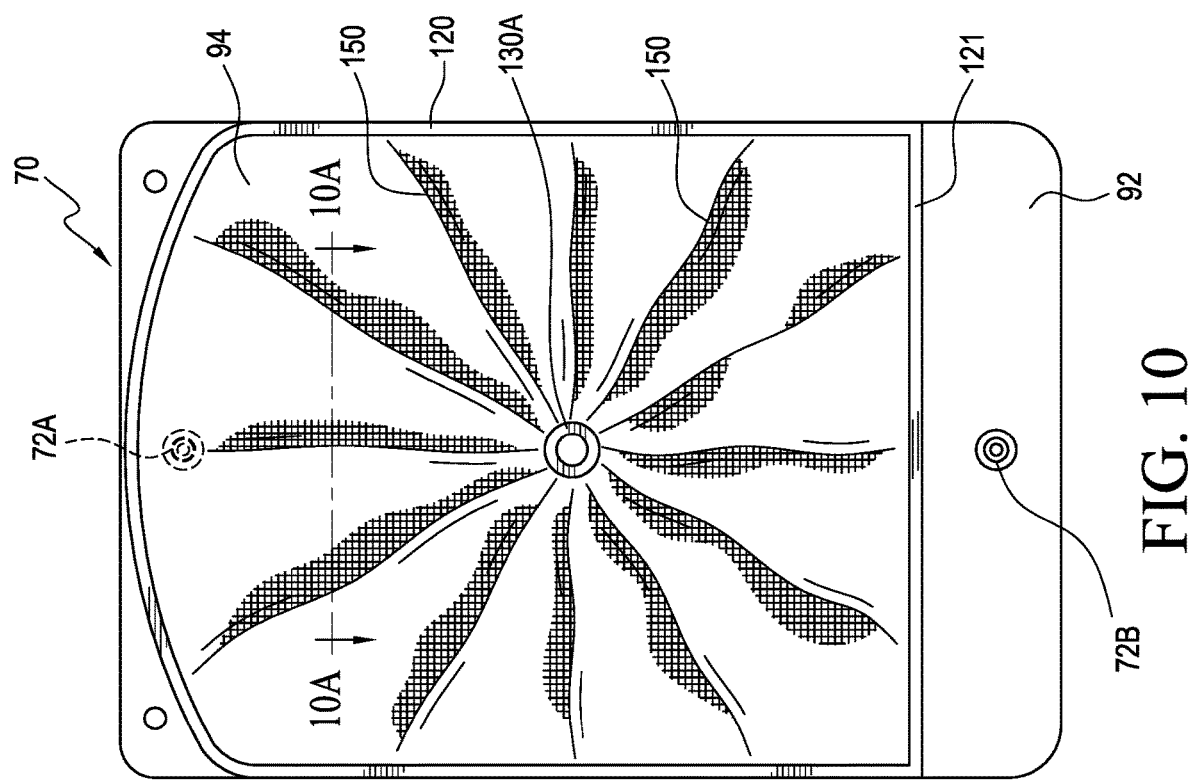
FIG. 10 is a top plan view of the filter sheet and back sheet shown in FIG. 9 with the bag assembly at least partially filled.

More specifically, FIG. 9 is a top plan view of filter sheet 94 overlaying second sheet 92 when bag 70 is empty. In this state, filter sheet 94 is substantially flat. In contrast, FIG. 10 is a top plan view of filter sheet 94 overlaying second sheet 92 when pre-filter compartment 126 (FIG. 8) of bag 70 is at least partially filled with microcarriers. In this state, the presence of retention seal 130A centrally securing filter sheet 94 to second sheet 92 causes a plurality of creases 150 to be formed on filter sheet 94. Creases 150 typically radially outwardly project from retention seal 130A. However, based on the configuration of retention seal 130A and the position and shape of other retention seals 130 concurrently used, the orientation of creases 150 can be altered. Furthermore, creases 150 are typically only formed to about the height of the microcarriers collected within pre-filter compartment 126. Thus, if microcarriers are collected to the level of retention seal 130A, creases may be formed at and below retention seal 130A but may not be formed above retention seal 130A. FIG. 10A is a cross sectional view of filter sheet 94 taken along section line 10A-10A in FIG. 10 that more clearly shows creases 150. Each crease 150 partially bounds a fluid channel 152 along which the culture solution can pass.

For example, with reference to FIG. 8, even if filter sheet 94 stretches out to contact interior surface 101 of first sheet 90 as a result of the collection of the microcarriers, the culture solution within post-filter compartment 128 can still freely pass between filter sheet 94 and first sheet 90 by traveling along fluid channels 152 formed by creases 150. Accordingly, the use of one or more retention seals 130 can increase fluid flow through bag 70, especially as microcarriers build up within bag 70, thereby decreasing processing and production time. The number, depth, orientation and other properties of creases 150 can vary based on the location, shape, and size of retention seals 130, the amount of microcarriers disposed within pre-filter compartment 126 and other variables.

The above discussed method is only example of how bag assembly 22 can be manufactured. It is appreciated that there are a variety of other methods that can be used to form bag assembly 22. By way of example and not by limitation, in contrast to just forming seal line 121 and retention seal 130A when filter sheet 94 overlays second sheet 92, as depicted and discussed with regard to FIG. 9, a seal line 120 in the form a continuous loop, as depicted in FIG. 10 can be formed between filter sheet 94 and second sheet 92. Seal line 120 includes seal line 121 and forms a perimeter edge of pre-filter compartment 126 between filter sheet 94 and second sheet 92, as previously discussed. Once seal line 120 is formed, first sheet 90 can be overlaid on filter sheet 94, as previously discussed. Seal line 136, as previously discussed and shown in FIG. 5, can then be formed directly on top of portions of seal line 120 so as to again form bag assembly 22 as depicted in FIG. 8.

In another alternative, filter sheet 94 can be smaller than second sheet 92 so that some or all of the perimeter edges of filter sheet 94 are inwardly spaced from the perimeter edge of second sheet 92. Thus, as depicted in FIG. 11, seal line 120 formed between filter sheet 94 and second sheet 92 can be inwardly spaced from seal line 136 formed between first sheet 90 and second sheet 92. In this embodiment, none of seal line 136 may overlay or seal to filter sheet 94. Seal line 120 and all of the other seal lines discussed herein can be formed using the method as discussed above with regard to seal line 121.

In still another embodiment, in contrast to first sheet 90 and second sheet 92 comprising two separate sheets, first sheet 90 and second sheet 92 can comprise overlaying portions of a single continuous sheet that has been folded over. The single sheet can be folded side-to-side or top-to-bottom with filter sheet 94 placed between the overlapping portions. The same seal lines and retention seals can be formed as discussed above except that along the fold line the overlying portions of the sheet may not need to be sealed together because they are already integrally formed as one continuous sheet.

As depicted in FIG. 4, bag assembly 22 can further comprise a first fluid line 156A that couples with first port 72A and a second fluid line 156B that couples with second port 72B. Fluid lines 156A and 156B can comprise flexible tubing or other conduits. Once bag assembly 22 is formed, it can be sterilized such as by radiation or other conventional sterilization techniques.

During use, stand 20 is erected as depicted in FIG. 3 and is typically placed on a table or other support structure. Bag assembly 22A is then secured to front face 46 of support 26. Specifically, the free end of first fluid line 156A is passed through first opening 58 on support 26 while the free end of second fluid line 156B is passed through second opening 60 of support 26. Back face 78 of bag 70 is then placed against front face 46 of support 26 and bag 70 is secured to support 26. In the depicted embodiment, bag 70 can be secured to support 26 by passing pins 158A and 158B (FIG. 2) through attachment holes 88A and 88B (FIG. 5) of bag 70 and into mounting holes 57A and 57B (FIG. 3) on support 26. In other embodiments it is appreciated that a variety of different fasteners, clamps, hangers, hooks, and the like can be used to secure bag assembly 22A/bag 70 to support 26.

In the attached configuration, bag 70 is disposed at the same corresponding angle α as previously discussed with regard to support 26. Although bag assembly 22A/bag 70 could be laid horizontally or supported vertically during use, it has been found that improved fluid flow, and thus reduced processing time, is achieved when bag assembly 22A/bag 70 is retained at the angle α during use. It is appreciated that bag assembly 22A can be used without stand 20 and that stand 20 can have a variety of different configuration, such as being in the form of other stands, mounts, racks, hangers or the like, that support and hold bag assembly 22A at the desired orientation.

Once bag assembly 22A is secured to stand 20, the free end of first line 156A can be fluid coupled to bioreactor 12 while the free end of second line 156B can also be fluid coupled to bioreactor 12 or can be fluid coupled to a separate container or other processing equipment. When it is desired to separate the microcarriers from the culture solution, the combined microcarriers and culture solution are dispensed from bioreactor 12 so that they travel though first line 156A and through first port 72A into pre-filter compartment 126 of bag 70. As previously discussed, the microcarriers are retained within pre-filter compartment 126 because they cannot pass through filter sheet 94. However, the culture solution which includes the cells and nutrient medium, travel through filter sheet 94 into post-filter compartment 128 and then out of bag 70 through second port 72B. Second line 156B then carries the culture solution back to bioreactor 12 or to some other container or processing equipment. Once the microcarriers are collected within pre-filter compartment 126, bag 70 can be used to transport the microcarriers either for disposal or for cleaning and reuse.

Figure 12:
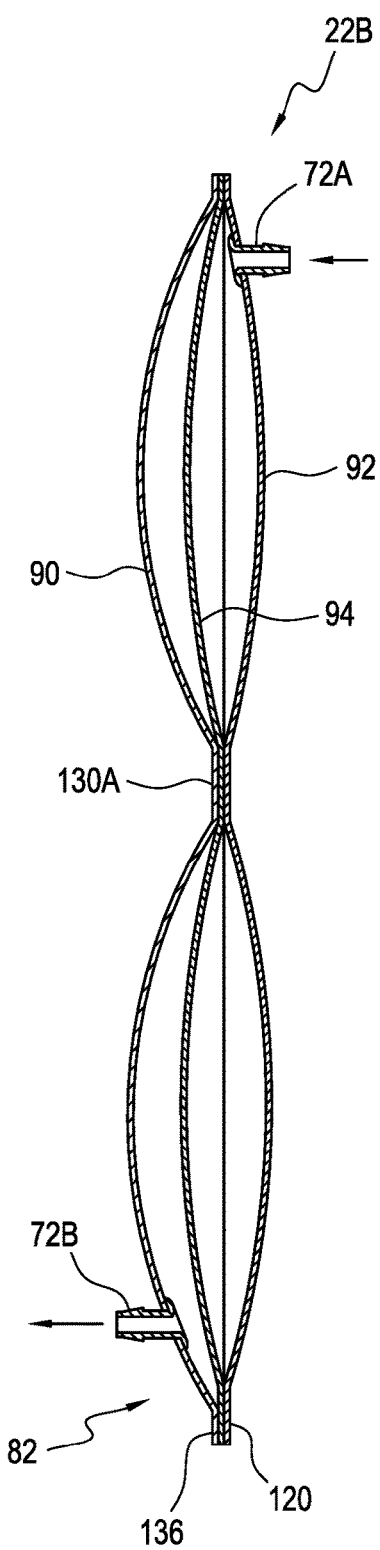
FIG. 12 is a cross sectional side view of an alternative embodiment of the bag assembly shown in FIG. 8.

In alternative embodiments, it is appreciated that bag assembly 22A can have a variety of different configurations. For example, depicted in FIG. 12 is a cross sectional side view of an alternative embodiment of a bag assembly 22B wherein like elements between bag assembly 22A an 22B are identified by like reference characters. It was previously discussed with regard to bag assembly 22A that first sheet 90 was directly welded to second sheet 92 at lower end 82 around second port 72B. In contrast, however, in bag assembly 22B the seal line 136 which is used to secure first sheet 92 to second sheet 92 is overlaid entirely on top of seal line 120 so that filter sheet 94 is always disposed between first sheet 90 and second sheet 92. Also in this embodiment, second port 72B is secured to first sheet 90 at lower end 82 as opposed to being secured to second sheet 92.

Bag assembly 22B also includes retention seal 130A. However, in contrast to retention seal 130A only being formed between second sheet 92 and filter sheet 94, in bag assembly 22B retention seal 130A secures together first sheet 90, second sheet 92 and filter sheet 94. This can be accomplished in one step by simultaneously welding together all three sheets or by first welding together two of the sheets, such as sheets 92 and 94, and then subsequently welding the third sheet thereto. Again, any desired size, shape, or number of retention seals 130 can be formed on bag assembly 22B.

In another alternative embodiment, in contrast to securing ports 72A and 72B directly to first sheet 90 and/or second sheet 92, it is appreciated that filter sheet 94 could be secured to first sheet 90 and/or second sheet 92. Ports 72A and/or 72B could then be passed through holes 116 that are formed through the sealed together filter sheet 94 with first sheet 90 or second sheet 92. Ports 72A and 72B would then be secured to filter sheet 94.

Although bag assemblies 22A and 22B only show the use of one inlet port 72A and one outlet port 72B, in other embodiments, at least two, three or more inlet ports 72A could be formed on the bag assembly and/or at least two, three, or more outlet ports 72B could be formed on the bag assembly.

Figure 13:
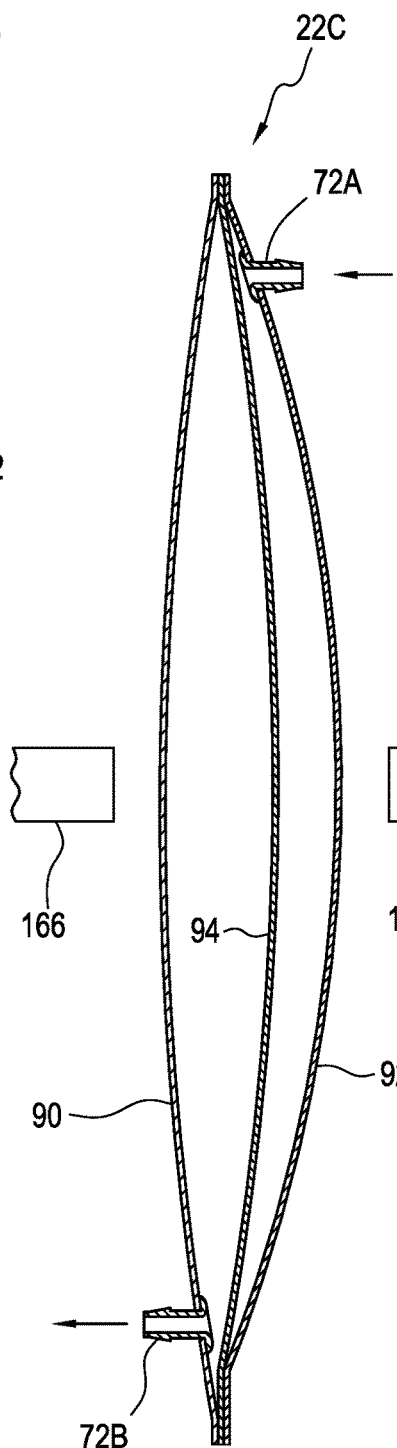
FIG. 13 is a cross sectional side view of an alternative embodiment of the bag assembly shown in FIG. 8 which is used with opposing structures to form a retention seal.
Figure 14:
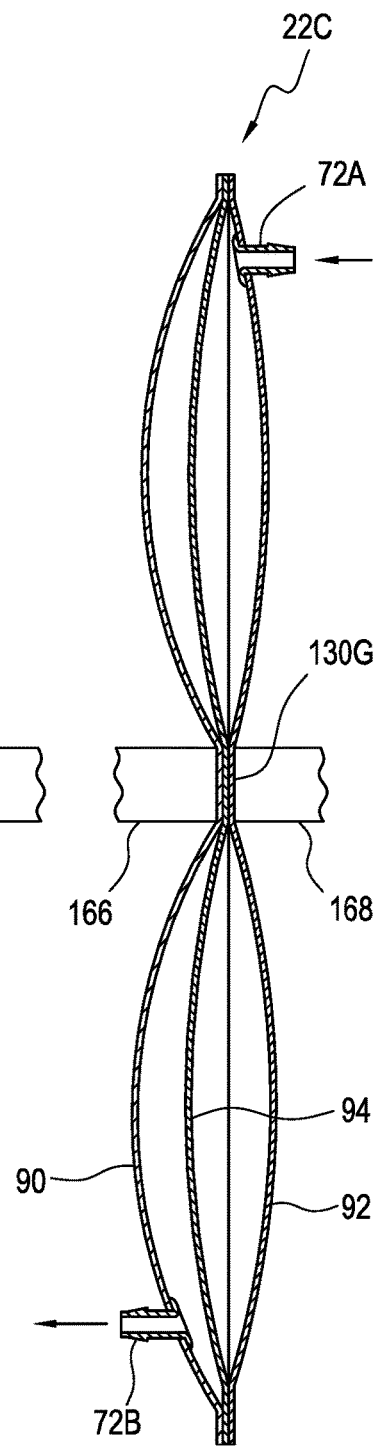
FIG. 14 is a cross sectional side view of the bag assembly shown in FIG. 13 with the opposing structures pressed together to mechanically form the retention seal.

Depicted in FIGS. 13 and 14 is another alternative embodiment of a bag assembly 22C wherein like elements between bag assembly 22A and bag assembly 22C are identified by like reference characters. Bag assembly 22C can be the same as bag assembly 22A or 22B except that in contrast to forming retention seal 130 by welding or using an adhesive to secure together sheets 92 and 94 or the combination of sheets 90, 92 and 94, a retention seal 130G can be formed by simply mechanically holding together sheets 90, 92 and 94. For example, a first structure 166 and a second structure 168 can be placed on opposing sides of bag assembly 22C. When in use, structures 166 and 168 can be pressed together so that portions of sheets 90, 92 and 94 are mechanically sandwiched and held together so as to form retention seal 130G. When no longer is use, structures 166 and 168 can be separated so that sheets 90, 92 and 94 can freely separate, thereby removing retention seal 130G. In one embodiment, structure 168 could simply comprise support 26.

Embodiments of the present invention have a number of unique benefits. For example, bag assemblies 22 are inexpensive to produce and are disposable after a singe use so that no cleaning is required. Furthermore, the bag assemblies enable a high fluid flow rate, even as the bag assemblies become filled with microcarriers, thereby decreasing processing time and improving efficiency. Other benefits are also achieved.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for filtering microcarriers from a liquid solution comprising cells, the method comprising:
    delivering the liquid solution with the microcarriers into a main compartment of a filter bag assembly, the filter bag assembly comprising:
        a flexible bag bounding the main compartment;
        a porous filter sheet disposed within the main compartment of the flexible bag and dividing the main compartment into a first compartment and a second compartment; and
        a first retention seal securing a portion of the porous filter sheet to a portion of the flexible bag within the main compartment so that at least a portion of the main compartment encircles the first retention seal; and passing the liquid solution through the porous filter sheet within the main compartment of the flexible bag, the porous filter sheet being configured so that the microcarriers cannot pass therethrough, wherein as the microcarriers are collected within the main compartment of the filter bag, a plurality of creases are formed on the filter sheet by the first retention seal.

2. The method as recited in claim 1, wherein the creases radially outwardly project from the first retention seal.

3. The method as recited in claim 1, wherein a fluid channel is bounded between an adjacent pair of the creases through which the liquid solution flows.

4. The method as recited in claim 1, wherein the microcarriers comprise beads having a diameter in a range between about 130 microns and about 300 microns.

5. The method as recited in claim 1, wherein prior to delivering the liquid solution, positioning the filter bag assembly on a stand so that the filter bag assembly is inclined at an angle in a range between 15° and 75° relative to horizontal.

6. The method as recited in claim 1, wherein the liquid solution with the microcarriers is delivered from a bioreactor that is fluid coupled with the flexible bag.

7. The method as recited in claim 1, further comprising:
the liquid solution with the microcarriers is delivered into the main compartment through a first port secured to the flexible bag; and
the liquid solution without the microcarriers is removed from the flexible bag through a second port secured to the flexible bag.

8. The method as recited in claim 1, wherein an outer perimeter edge of the first retention seal is circular.

9. The method as recited in claim 1, wherein the first retention seal has the configuration of a ring.

10. The method as recited in claim 1, further comprising a second retention seal spaced apart from the first retention seal and securing the porous filter sheet to a portion of the flexible bag.

11. The method as recited in claim 1, wherein the flexible bag comprises:
a flexible first sheet; and
a flexible second sheet overlying and secured to the first sheet so that the main compartment is formed therebetween;
wherein the first compartment and the second compartment are entirely disposed on opposing sides of the porous filter sheet.

12. The method as recited in claim 11, further comprising:
a first port secured to the first sheet or the second sheet and communicating directly with the first compartment, the liquid solution with the microcarriers being delivered into the first compartment through the first port; and
the first retention seal securing the second sheet to the filter sheet so that at least a portion of the first compartment bounded between the second sheet and the filter sheet encircles the first retention seal.

13. The method as recited in claim 12, further comprising a second port secured to the first sheet or the second sheet and communicating directly with the second compartment, the second port being spaced apart from the first retention seal so that the second port is not encircled by the retention seal, the liquid solution without the microcarriers being removed from the flexible bag through the second port.

14. The method as recited in claim 11, wherein the first sheet and the second sheet are secured together by a first seal line that encircles the main compartment in a continuous loop, the first retention seal being spaced apart from the first seal line.

15. The method as recited in claim 14, wherein the porous filter sheet is secured to the second sheet by a second seal line that encircles a portion of the porous filter sheet, the first retention seal being spaced apart from the second seal line.

16. A method for filtering microcarriers from a liquid solution comprising cells, the method comprising:
passing the liquid solution with the microcarriers from a bioreactor into a first compartment of a filter bag assembly, the filter bag assembly comprising:
a flexible bag bounding a main compartment;
a porous filter sheet disposed within the main compartment of the flexible bag and dividing the main compartment into the first compartment and a second compartment; and
a first retention seal securing a central portion of the porous filter sheet to a portion of the flexible bag within the main compartment;
passing the liquid solution from the first compartment to the second compartment so as to pass through the porous filter sheet, the porous filter sheet being configured so that the microcarriers cannot pass through the porous filter sheet and are collected within the first compartment; and
removing the liquid solution without the microcarriers from the second compartment,
wherein as the microcarriers are collected within the first compartment of the filter bag, a plurality of creases are formed on the filter sheet by the first retention seal.

* * * * *